United States Patent [19]

Bimber et al.

[11] 4,286,091

[45] Aug. 25, 1981

[54] SYNTHESIS OF PYRIDAZINONE PHARMACEUTICAL INTERMEDIATES USING DIKETENE REACTANT

[75] Inventors: Russell M. Bimber, Painesville; Russell Buchman, Madison; Michael F. DePompei, Mentor; Larry J. Powers, Madison, all of Ohio

[73] Assignee: Diamond Shamrock Corporation, Dallas, Tex.

[21] Appl. No.: 151,395

[22] Filed: May 19, 1980

[51] Int. Cl.$^3$ ............................................ C07D 237/14
[52] U.S. Cl. .................................... 544/239; 568/335; 568/337
[58] Field of Search ........................................ 544/239

[56] References Cited
FOREIGN PATENT DOCUMENTS 2705562 8/1978 Fed. Rep. of Germany .

OTHER PUBLICATIONS

Radte et al., Chem. Abs. 89, 215429V (1978).

*Primary Examiner*—Mark L. Berch
*Attorney, Agent, or Firm*—Stuart L. Melton; Walter C. Danison, Jr.

[57] ABSTRACT

Valuable pyridazinone intermediates to pharmaceutically useful compounds can be prepared in surprisingly high yields by the reaction of the corresponding monohydrazone with diketene, preferably in the presence of a basic catalyst. In an especially preferred embodiment, p,p'-dichlorobenzil monohydrazone and diketene are reacted in a xylene solvent in the presence of triethylamine to afford 4-acetyl-5,6-bis(p-chlorophenyl)-2H-pyridazin-3-one, which can then be reacted with ethylene carbonate in the presence of potassium carbonate to afford the antihypertensive agent, 4-acetyl-5,6-bis(p-chlorophenyl)-2-(2'-hydroxyethyl)-2H-pyridazine-3-one.

21 Claims, No Drawings

SYNTHESIS OF PYRIDAZINONE PHARMACEUTICAL INTERMEDIATES USING DIKETENE REACTANT

TECHNICAL FIELD OF THE INVENTION

The present invention provides an improved process for the synthesis of pyridazinones which are valuable intermediates to pharmaceutically useful compounds, said process comprising the reaction of the corresponding monohydrazone with diketene, preferably in the presence of a basic catalyst.

BACKGROUND OF THE PRIOR ART

Substituted pyridazinone compounds having various substituents have heretofore been prepared and proposed for use in a wide range of different ultimate applications. Thus, for example, U.S. Pat. Nos. 3,657,242; 3,689,652; 3,746,712; 3,812,256; 3,822,260; 3,876,786; 3,876,787; 3,931,177; and 3,975,388 disclose a variety of pharmacologically active 4,5-dihydropyridazinones. As a chemical class, those compounds comprise dihydro (saturated)ketopyridazines.

Representative of another class of related compounds are the pyridaz-3-one compounds disclosed in U.S. Pat. No. 2,839,532. The aforesaid patent is directed to 4,5-unsaturated pyridaz-3-one (or 3-ketopyridazine) compounds having a cyano, acetyl, carboxyl, carbethoxy or benzoyl group in the 4- position optionally substituted in the 5,6-positions by lower alkyl, phenyl or substituted phenyl residues. These compounds are disclosed as being useful as medicaments, particularly, analgesics, anesthetics, antibacterials or disinfectants.

U.S. Pat. No. 3,491,096 and British Pat. No. 840,522 are directed to other previously investigated pyridazone compounds. The aforementioned British patent pertains to 2-hydroxymethyl-6-phenyl-3-pyridazone and the analgesic utility thereof. U.S. Pat. No. 3,491,096 describes 2-pyridylalkylated-6-phenylpyridaz-3-one compounds possessing sedative, analgesic and antispasmodic properties, with occasional hypotensive effects being observed.

Copending Powers et al U.S. patent application Ser. No. 11,416, U.S. Pat. No. 4,238,490 filed Feb. 12, 1979, and assigned to the assignee hereof, describes novel pyridazin(2H)-3-ones of the general formula

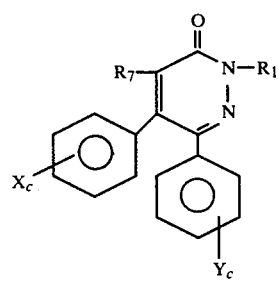

(I)

and pharmaceutically acceptable nontoxic salts thereof wherein $R_1$ is hydrogen, $C_1-C_4$ hydroxyalkyl, $C_1-C_4$ carbamylmethyl, $C_1-C_6$ carboxyalkyl, $C_1-C_6$ alkoxycarbonyl($C_1-C_6$)alkyl, $C_1-C_6$ alkoxy($C_1-C_6$) alkyl; or the group

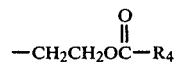

where a is 1 to 4, inclusive, $R_2$ is hydrogen or $C_1-C_4$ alkyl and $R_3$ is amino, methylthio, $C_1-C_6$ alkylamino, $C_1-C_6$ alkylimino, $c_1-C_6$ acylamino, $C_1-C_6$ alkoxycarbonylamino, morpholinyl, piperazinyl, ($C_1-C_6$ alkoxycarbonyl)piperazinyl, piperidinyl, pyrrolidinyl, glucuronyl or glucopyranosyl; or the group

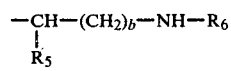

where $R_4$ is hydrogen, $C_1-C_{20}$ alkyl, $C_1-C_6$ carboxyalkyl, phenyl, phenyl($C_1-C_6$)alkyl, or $R_4$ represents the group

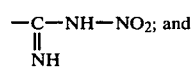

where b is 0 to 4, inclusive, $R_5$ is hydrogen, $C_1-C_4$ alkyl, methylthioethyl, benzyl, $NH_2$, or benzyloxycarbamyl, and $R_6$ is hydrogen, benzyloxycarbonyl, t-butyloxycarbonyl or $$-\underset{\underset{NH}{\|}}{C}-NH-NO_2; \text{ and}$$

$R_7$ is acetyl, cyano, phenylsulfonyl, ($C_1-C_4$)alkylhydrazono, naphthyl, phenyl or phenyl substituted with at least one substituent selected from the group consisting of halogen, $C_1-C_6$ alkylamino and $C_1-C_4$ alkoxy; and $X_c$ and $Y_c$ are the same or different and are independently selected from the group consisting of halogen, $C_1-C_4$ alkyl and $C_1-C_4$ alkoxy where c is 0, 1 or 2; subject to the provisos that when $R_7$ is acetyl, phenyl or cyano, $R_1$ is other than hydrogen; and when $R_7$ is cyano, $R_1$ is $C_1-C_4$ hydroxyalkyl, $C_1-C_6$ carboxyalkyl of the group

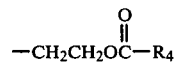

where $R_4$ is $C_1-C_6$ carboxyalkyl and $X_c$ and $Y_c$ are halo, with c being at least 1;

and the enol tautomeric derivatives and metabolites thereof. Said compounds are useful therapeutic antihypertensive agents, as described in the aforesaid U.S. application Ser. No. 11,416, now U.S. Pat. No. 4,238,490 said application being hereby incorporated by reference in its entirety and relied upon.

As used throughout the instant specification and claims, the expressions "alkyl" and "alkoxy" are inclusive of straight and branched chain carbon-carbon linkages, e.g., methyl, ethyl, n-propyl, isopropyl, n-butyl, isobutyl, sec-butyl, tert-butyl, isohexyl, etc. The expression "acyl" includes, e.g., formyl, acetyl, propionyl, butanoyl, pentanoyl, hexanoyl and the like. The term "halo" includes chlorine, fluorine, bromine and iodine. The expression "pharmaceutically acceptable nontoxic salts," as used herein, is intended to include those salts capable of being formed with the compounds of formula (I) without materially altering the chemical structure or pharmacological properties of the parent compounds. Representative of acids for reaction with sufficiently basic pyridazinone derivatives include hydrochloric, hydrobromic, hydroiodic, nitric, phosphoric, citric, etc. Alkali metal salts of carboxylic acid derivatives of formula (I) may be obtained by reaction with suitable bases, e.g., sodium hydroxide, potassium hyroxide, etc. Alkaline earth metal salts may be similarly obtained. Additionally, compounds of formula (I) containing amino acid residues, i.e., an α-amino acyl group, may be obtained as their hydrate salts such as mono- or di-hydrobromide, hydrochloride, etc., hydrate and such inorganic and organic acid addition salts of certain of the compounds of formula (I) and amino acid residues or derivatives may advantageously be employed to, for instance, alter solubility properties or augment bioavailability.

As will be apparent to those skilled in the art, the keto compounds of formula (I) wherein $R_1$ is hydrogen may be present in the enol tautomeric form. It is also noted that certain of the $R_1$ substituents at the 2-position, e.g., hydroxyalkyl, carboxyalkyl, alkoxycarbonylalkyl, alkoxyalkyl, alkylaminoalkyl, glucuronyl, etc., constitute possible enolic derivatives and/or metabolites of compounds within the scope of the present invention.

U.S. application Ser. No. 11,416, now U.S. Pat. No. 4,238,490 teaches that the subject pyridazinones, i.e., substituted keto-pyridazine compounds of formula (I), may be prepared by various alternative methods theretofore employed in the synthesis of other pyridazinone compounds (e.g., in U.S. Pat. No. 2,839,532) or modifications thereof to obtain the $R_1$, $R_7$, $X_c$ or $Y_c$ substituents thereon as defined above. In general, one method for the preparation of pyridazin(2H)-3-ones comprises reacting an appropriately substituted monohydrazone, with the appropriately substituted acetic acid ester or reacting the appropriately substituted benzil and appropriately substituted hydrazide under cyclization conditions, e.g., in the presence of suitable solvents, such as xylene, acetonitrile, methanol, benzene, etc., and alkaline condensing agents, such as hydroxides, alcoholates, hydrides, alkali or alkaline earth metals, tertiary amines, etc., to effect ring closure. The foregoing general reaction scheme may be depicted as follows

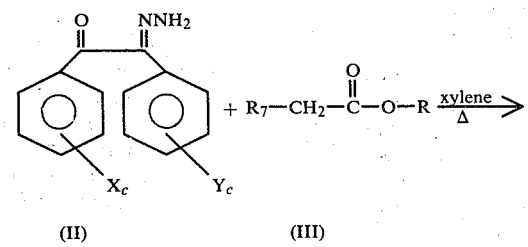

(II)   (III)

-continued

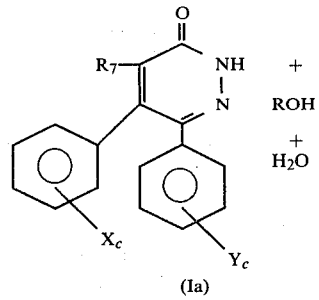

(Ia)

wherein R is typically an alkyl group and $R_7$ is not here restricted by the provisos set forth earlier. As will be apparent from the foregoing description of the formula (I) substituents, the formula (Ia) products are in some instances pharmacologically active compounds of formula (I), while in other instances the formula (Ia) products are intermediates which can be converted by subsequent reactions to the compounds of formula (I).

The monohydrazone reactants may be prepared by the reaction of an appropriate substituted benzil with hydrazine hydrate. Suitable benzil starting materials may be obtained commercially or prepared by known methods, for example, cyanide ion catalyzed benzoin condensation followed by oxidation. The pyridazin(2H)-3-one compounds thus prepared may be utilized following suitable recrystallization/purification as intermediates for the preparation of further 2-substituted derivatives in accordance with the above $R_1$ definition.

Exemplary of preferred compounds for use in the antihypertensive compositions and methods of U.S. Ser. No. 11,416 now U.S. Pat. No. 4,238,490 are compounds of the above general formula (I) wherein, correspondingly, $R_1$ represents $C_1$–$C_4$ hydroxyalkyl (especially, hydroxyethyl), esters thereof, e.g., acetate, butyrate, propanoate, formate, hemisuccinate, octadecanoate, benzoate, etc.; amino acid esters thereof corresponding to the

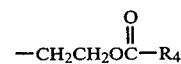

group defined hereinabove wherein $R_4$ represents

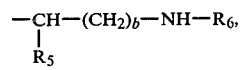

e.g., lysine, glycine, methionine, phenylalanine, etc.; or where $R_1$ is $C_1$–$C_4$ carbamylmethyl, e.g., α-acetamido; aminoalkyl, e.g., aminometyl, aminoethyl, etc.; $C_1$–$C_6$ alkylaminoethyl, e.g., dimethylaminoethyl; glucopyranosyl; glucuronyl; 1-morpholinylethyl; 1-piperidinylethyl; 1-pyrrolidinylethyl and acetamidoethyl; and wherein $R_7$ represents acetyl and $X_c$ and $Y_c$ are para-halo, preferably para-chloro. An especially preferred antihypertensive agent provided by U.S. Ser. No. 11,416, now U.S. Pat. No. 4,238,490 is 4-acetyl-5,6-bis(p-chlorophenyl)-2-(2'-hydroxyethyl)-2H-pyridazin-3-one. According to the methods described in Ser. No. 11,416 U.S. Pat. No. 4,238,490, that compound is prepared by first reacting ethanol and sodium to form sodium ethoxide, then adding ethyl acetoacetate and p,p'- dichlorobenzil monohydrazone, to afford 4-acetyl-5,6-bis(p-chlorphenyl)-2H-pyridazin-3-one in 20% yield. That intermediate is then reacted with ethylene carbonate and potassium hydroxide in dimetylformamide to afford the desired final product. The intermediate 4-acetyl-5,6-bis(p-chlorophenyl)-2H-pyridazin-3-one can be used to prepare other antihypertensive compounds of Ser. No. 11,416 U.S. Pat. No. 4,238,490 as well. See, for example, Examples 9, 10 and 11 therein. However, the poor yields heretofore obtained in the preparation of that key intermediate have been a serious problem standing in the way of commercialization of the final antihypertensive products such as 4-acetyl-5,6-bis(p-chlorophenyl)-2-(2'-hydroxyethyl)-2H-pyridazin-3-one.

In view of the foregoing, it is apparent that a serious need exists for an improved process for the preparation of the antihypertensive agents of formula (I) and intermediates thereto.

SUMMARY OF THE INVENTION

It is therefore a primary object of the present invention to provide an improved process for the preparation of the antihypertensive agents of formula (I) and intermediates thereto. More particularly, it is a primary object of the present invention to provide an improved process for the preparation of compounds of the formula

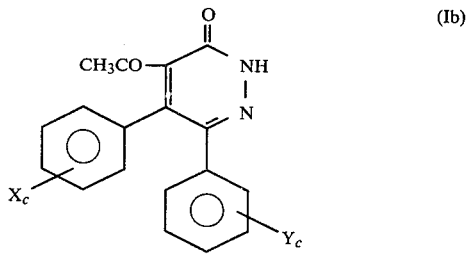

wherein $X_c$ and $Y_c$ are defined as hereinabove, in substantially higher yields than heretofore possible, thus affording a commercially viable route to the corresponding preferred antihypertensives of formula (I).

These and similar objects are accomplished according to the present invention by the reaction of a monohydrazone of formula (II) above with diketene, to afford the corresponding compound of formula (Ib).

DETAILED DESCRIPTION OF THE PREFERRED EMBODIMENTS

Preferred monohydrazones of formula (II) for use in the instant process are those wherein $X_c$ and $Y_c$ are para-halo, a particularly preferred monohydrazone starting material being p,p'-dichlorobenzil monohydrazone. The other reactant employed in the instant process is, as indicated above, diketene, which is also known as acetyl ketene and which can be represented by the structural formula

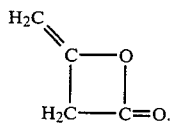

The reactants are conveniently combined in a suitable organic solvent, for example xylene or toluene. Generally speaking, the solvent of choice is xylene, but other useful solvents will be apparent to those skilled in the art. Advantageously, the reaction is conducted at elevated temperature, preferably at the reflux temperature. In addition, the reaction is most preferably carried out in the presence of a suitable basic catalyst. Especially useful catalysts include triethylamine and tetramethylethylenediamine, the use of either of which has been found to result in particularly high yields of the desired product. In general, triethylamine is considered the catalyst of choice. However, satisfactory yields may be obtained without use of any catalyst, although a greater amount of diketene reactant is generally required.

It has surprisingly been found that the instant diketene process is vastly superior to the alkyl acetoacetate process typically used in the prior art. Thus, only 20% yields of 4-acetyl-5,6-bis(p-chlorophenyl)-2H-pyridazin-3-one are reported in U.S. Ser. No. 11,416 now U.S. Pat. No. 4,238,490 for the reaction of ethyl acetoacetate with p,p'-dichlorobenzil monohydrazone, using sodium ethoxide reagent to effect ring closure. Similarly, it has more recently been found that the reaction of methyl acetoacetate with the aforesaid monohydrazone, using pyridine as the condensing agent, affords the desired 4-acetyl-5,6-bis(p-chlorophenyl)-2H-pyridazin-3-one in less than 35% yield. In contrast, yields of up to about 75% of the aforesaid key intermediate have been obtained when using the diketene process of the present invention. It has also surprisingly been found that, when triethylamine is employed as a catalyst, the instant diketene/triethylamine process requires only half as much catalyst as the methyl acetoacetate/pyridine process discussed supra. This and other advantages of the instant process are evident from the table below.

| COMPARISON OF DIKETENE AND METHYL ACETOACETATE PROCESSES | | |
| --- | --- | --- |
| | DIKETENE | METHYL ACETOACETATE |
| Percent Yield | 68–75 | 10–60 |
| Quality of A[a] | 99.5% without recrystallization | 99.5% with recrystallization |
| Catalyst Usage (lbs/lb B[b]) | 0.22[c] | 0.44[d] |
| Monohydrazone Usage (lbs/lb B[b]) | 1.43 | 1.89 |
| Diketene or Methyl Acetoacetate (lbs/lb B[b]) | 0.45 | 0.76 |

[a]A is the key intermediate, 4-acetyl-5,6-bis(p-chlorophenyl)-2H-pyridazin-3-one.
[b]B is the antihypertensive final product, 4-acetyl-5,6-bis-(p-chlorophenyl)-2-(2'-hydroxyethyl)-2H-pyridazin-3-one.
[c]Triethylamine.
[d]Pyridine.

In order to obtain optimum yields in the process of the present invention, an appropriate catalyst as indicated above, preferably triethylamine, is employed. The catalyst should be added after the reaction temperature has reached 100° C. or greater and the diketene addition is to be initiated. Addition of catalyst considerably in advance of the diketene addition has been found to result in decomposition of the monohydrazone reactant. Also, the manner in which diketene is added to the reaction mixture is important. Diketene can "crack" to ketene and, in fact, the acyl derivative from reaction of ketene and monohydrazone can be a major by-product of the instant process. Accordingly, addition of the diketene should be made close to the surface of the liquid. Significant decreases in yield, of the order of 12%, have been observed when the diketene has been allowed to run down the walls of the reaction vessel.

The optimum amount of catalyst employed in the instant process will vary with the particular catalyst and reactants used, as well as with reaction conditions. In a preferred embodiment of the process of the present invention, wherein p,p'-dichlorobenzil monohydrazone and diketene are refluxed in xylene solvent in the presence of triethylamine, a preferred level of 0.2 ml of triethylamine/g of monohydrazone has been established. The use of 0.3 ml/g resulted in no better yields. However, when 0.1 ml/g was used, it was necessary to increase reaction time from 2 to 2.5 hours in order to obtain comparable yields.

The time required for complete conversion of monohydrazone is about two hours, using triethylamine catalyst in refluxing xylene. Beyond that time, generally no further reaction takes place. However, as indicated above, longer reaction times are necessary when lower levels (e.g., 0.1 ml/g) of triethylamine are used. Also, reaction times will vary depending on the particular catalyst employed. Longer reaction times would also be expected when the reaction is conducted in the absence of catalyst.

The process of the present invention is relatively insensitive to impurities in the monohydrazone reactant. However, if a significant amount of residual hydrazine is present, (e.g., on the order of 2.5% by weight), then a dramatic reduction in yield will be observed.

Because 4-acetyl-5,6-bis(p-chlorophenyl)-2H-pyridazin-3-one is the immediate precursor to the desired antihypertensive agent 4-acetyl-5,6-bis(p-chlorophenyl)-2-(2'-hydroxyethyl)-2H-pyridazin-3-one, a high degree of purity of the precursor is required. Therefore, a particular advantage of the present process is the fact that the crystalline 4-acetyl-5,6-bis(p-chlorophenyl)-2H-pyridazin-3-one obtained directly from the process is of sufficiently high purity (99.5%) that recrystallization is not necessary. Thus, the preferred product of the instant process, i.e., 4-acetyl-5,6-bis(p-chlorophenyl)-2H-pyridazin-3-one, can be converted directed to the antihypertensive agent 4-acetyl-5,6-bis(p-chlorophenyl)-2-(2'-hydroxyethyl)-2H-pyridazin-3-one, preferably by reaction with ethylene carbonate in dimethylformamide solvent in the presence of trace quantities of potassium carbonate at about 85° C., followed by crystallization from ethyl acetate.

Without further elaboration, it is believed that one of ordinary skill in the art can, using the preceding description, utilize the present invention to its fullest extent. Consequently, the preferred specific embodiments set forth below are to be construed as merely illustrative and not limitative of the remainder of the specification and claims in any way whatsoever.

In the Examples which follow, it is to be noted that Examples 1-3 are illustrative of starting material preparations; Examples 4 and 5 are comparative examples of the procedures used and yields obtained previously; Examples 6-11 are illustrative of the improved process of the present invention; and Example 12 is illustrative of methods for converting a product of the instant process into an antihypertensive agent of formula (I).

EXAMPLE 1

A 20 gallon (approximately 76.9 liter) reaction vessel was charged with 22.7 kg of p-chlorobenzaldehyde and the solids were blanketed with nitrogen. 12.6 Liters of methanol were added, and the resultant mixture was agitated and heated. When the temperature reached 50° C., the solids had dissolved and 6.0 liters of distilled water were added. Heating was continued until the temperature reached 79° C., at which time 544 g of potassium cyanide dissolved in 1.3 liters of water were added. The methanol began refluxing vigorously and the solution turned a bright orange color. The exothermic reaction was essentially complete within 30 minutes, but heating was continued at methanol reflux temperature for an additional hour.

The reaction product was cooled to 50° C., 20 liters of cold water were added, and the mixture was agitated. Then the orange colored organic layer was allowed to settle and the water-methanol upper layer was removed under nitrogen. The organic layer was washed twice more with 8 liter portions of water, the final wash being carried out at 60° C. to prevent solidification of the organic layer. There was thus obtained the desired p,p'-dichlorobenzoin.

EXAMPLE 2

To the washed p,p'-dichlorobenzoin obtained in Example 1 were added 21.3 liters of glacial acetic acid. The mixture was agitated and heated to 97° C., then 13.7 kg of concentrated nitric acid were added over a one hour period. The reaction mixture was heated at 97°-100° C. for an additional six hours, an additional six liters of glacial acetic acid being added during the oxidation period to maintain fluidity of the thickening slurry.

After the oxidation was completed, the reaction mixture was cooled to 25° C. and transferred to a filter crock. The bright yellow-colored product was thoroughly washed with water. The washed product was divided into four portions, and each portion was returned to the reaction vessel and stirred with 10 gallons (approximately 38.5 liters) of an approximately 5% bicarbonate solution to neutralize any residual acids and to remove p-chlorobenzoic acid by-product.

The bicarbonate washed p,p'-dichlorobenzil was returned to the crock filter, washed thoroughly with water and dried overnight at 120° C. The weight of dried p,p'-dichlorobenzil was 17.5 kg, a 77% yield based on the amount of p-chlorobenzaldehyde charged in Example 1.

EXAMPLE 3

A 20 gallon (76.9 liter) reaction vessel was charged with 5.0 kg of p,p'-dichlorobenzil and 37 liters of isopropyl alcohol. The mixture was agitated and heated to 85° C., then 1.03 kg of 85% hydrazine hydrate were added. Within twenty minutes, the slurry became a clear solution. An additional 200 g of hydrazine hydrate were then added. Within 30 minutes after the second hydrazine addition, the desired p,p'-dichlorobenzil monohydrazone began to precipitate and to form a thick slurry. The slurry was stirred for one additional hour at 85°-90° C., then was cooled to 25° C. The monohydrazone was transferred to a filter crock and washed with isopropyl alcohol. The washed monohydrazone was returned to the reaction vessel, 25 liters of isopropyl alcohol were added and the mixture was heated to 80° C. with agitation. The reaction mixture was then cooled to 25° C., transferred to the filter crock, washed with isopropyl alcohol and dried overnight at 65° C. The total weight of dry p,p'-dichlorobenzil monohydrazone was 14.86 kg, an 81% yield based on the p,p'-dichlorobenzil.

EXAMPLE 4

Ethanol, dried by distilling from Mg-I₂, was added to a dry flask (N₂ atmosphere) containing clean sodium (1.1 equivalent). After the sodium had reacted, ethyl acetoacetate (7 ml) was added dropwise to the cold (0°–5° C.) alkoxide solution. p,p'-Dichlorobenzil monohydrazone (15 g) was added through a powder addition funnel. After heating the reaction mixture at reflux for three hours, it was cooled and poured into 1 N HCl. The resulting precipitate was separated by filtration and washed with water. The resulting product was recrystallized from ethanol-acetonitrile to give 4-acetyl-5,6-bis(p-chlorophenyl)-2H-pyridazin-3-one melting at 269°–271° C., in 20% yield.

Analysis—calculated for $C_{18}H_{12}Cl_2N_2O_2$ (%): C, 60.20; H, 3.34; N, 7.80. Found (%): C, 60.02; H, 3.33; N, 7.91.

EXAMPLE 5

A 20 gallon (76.9 liter) reaction vessel was charged with 34.2 liters of xylene and 13.76 kg of p,p'-dichlorobenzil monohydrazone. The mixture was heated up to 60° C. over a 20 minute period and 4.125 liters of pyridine were then added. Heating was continued for an additional 30 minutes, during which time the reaction temperature climbed to 110° C. 6.0 Kg of methyl acetoacetate diluted with 5.5 liters of xylene were then added. Water began to distill immediately. Over the next 5 hours, 1.25 liters of water were removed by azeotropic distillation. The temperature was then raised and 28.5 liters of pyridine and xylene were removed by distillation.

The reaction mixture was cooled to 40° C. and the solids were collected by filtration and washed, first with xylene and then with petroleum ether. The crude product was dried at 75° C. for 6 hours. There were thus obtained 5.845 kg of crude 4-acetyl-5,6-bis(p-chlorophenyl)-2H-pyridazin-3-one melting at 262°–270° C. (34.7% yield based on monohydrazone charged). The crude product was slurried in methanol to remove a red-brown colored solid which was soluble in the methanol. Total reaction time to convert the monohydrazone to the pyridazin-3-one was 10 hours, with an additional one hour for methanol wash and an additional 12 hours for drying time.

EXAMPLE 6

A flask equipped with a stirrer, thermometer, condenser, Dean Stark trap and additional funnel was charged with 50 g of p,p'-dichlorobenzil monohydrazone, then 120 ml of p-xylene were added. The resultant mixture was heated to 45° C., 15 ml of triethylamine were added, and that mixture was heated to the reflux temperature, with stirring. Then, 16 ml of diketene were added gradually over a 15 minute period, while maintaining the reaction mixture at the reflux temperature (119°–125° C.). Refluxing (at about 125° C.) was continued until thin layer chromatography indicated complete consumption of monohydrazone reactant (approximately 2 hours from the start of diketene addition). The reaction mixture was cooled and the crystalline material was removed by filtration, washed with methanol and dried. 44.0 g (71.7% yield) of the desired 4-acetyl-5,6-bis(p-chlorophenyl)-2H-pyridazin-3-one, melting at 270°–272° C., were obtained. 2 ml of water (66% of theory) were evolved during the process.

EXAMPLE 7

The procedure of Example 6 was repeated substantially as described therein, except that only 5 ml of triethylamine were used and refluxing was continued for approximately two and one-half hours after the start of diketene addition. 45.5 g (74.5% yield) of 4-acetyl-5,6-bis(p-chlorophenyl)-2H-pyridazin-3-one were obtained.

EXAMPLE 8

A flask equipped as in Example 6 was charged with 50 g of p,p'-dichlorobenzil monohydrazone, 100 ml of p-xylene and 10 ml of triethylamine. That mixture was heated to reflux, then a solution of 16 ml of diketene in 16 ml of p-xylene was added over a 5 minute period via a tube emptying immediately above the level of the reaction mixture in the flask. Refluxing was continued for a 2 hour period calculated from the beginning of the diketene addition. The reaction mixture was then cooled and filtered. The residue was dried to give 45 g (73% yield) of the desired 4-acetyl-5,6-bis(p-chlorophenyl)-2H-pyridazin-3-one.

EXAMPLE 9

A flask equipped with two Dean Stark traps, two condensers, two addition funnels and a stirrer was charged with 600 g of p,p'-dichlorobenzil monohydrazone and 1250 ml of xylene. The mixture was heated to 100° C., then heating was discontinued and the separate addition of a solution of 192 ml of diketene in 192 ml of xylene and a solution of 120 ml of triethylamine in 120 ml of xylene was begun. The two solutions were added at such a rate as to maintain the reaction mixture at reflux. (The addition occured over a 17 minute period.) Refluxing was continued until two hours and 10 minutes had elapsed from the beginning of the diketene addition. Then, the reaction mixture was cooled and 24 ml of water (66% of theory) were removed. The reaction mixture was filtered and the solid material was washed and dried to give 510 g (68.5% yield) of 4-acetyl-5,6-bis(p-chlorophenyl)-2H-pyridazin-3-one, melting at 264°–271° C.

The filtrate was allowed to stand overnight and the solids which formed were removed by filtration. Thus, there were recovered 30.0 g monohydrazone starting material, as identified by melting point and mixed melting point with authentic p,p'-dichlorobenzil monohydrazone. The yield of 4-acetyl-5,6-bis(p-chlorophenyl)-2H-pyridazin-3-one based on 570.0 g of monohydrazone actually consumed was 72.3%.

EXAMPLE 10

To a stirred and warm solution of 8.8 g (0.03 mole) of p,p'-dichlorobenzil monohydrazone and 300 ml of toluene was added 5.0 g (0.06 mole) of diketene dropwise over an approximately 5 minute period. The resulting solution was stirred under reflux in a reaction vessel equipped with a Dean Stark trap for 2 hours, then cooled slightly. 3 ml of N,N,N',N'-tetramethylethylenediamine were added dropwise and the reaction mixture was then refluxed for 23 hours, during which time approximately 0.38 ml of water was collected. The dark brown solution thus obtained was allowed to stand at room temperature for 20 hours, then was evaporated in vacuo to a yellow solid which was boiled with approximately 250 ml of ethyl acetate, cooled and filtered. The yellow solid obtained in this manner was air dried, affording 5.1 g of the desired 4-acetyl-5,6-bis(p-chlorophenyl)-2H-pyridazin-3-one, melting at 269°-272° C. The ethyl acetate filtrate was evaporated in vacuo, additional ethyl acetate was added at room temperature, and the mixture was cooled and filtered. The yellow solid thus obtained was air dried to give a second crop of the desired product, weighing 2.0 g and melting at 267°-269° C. A third crop, weighing 0.8 g, softening at 260° C. and melting at 264°-266° C., was obtained in an identical way. A fourth crop, weighing 0.4 g, softening at 263° C. and melting at 267°-270° C., was obtained from ethyl acetate/benzene solution. The total yield of 4-acetyl-5,6-bis(p-chlorophenyl)-2H-pyridazin-3-one was 77%.

EXAMPLE 11

To a warm and stirred solution of 1.0 g (3.4 mmole) of p,p'-dichlorobenzil monohydrazone and 30 ml of toluene was added a solution of 0.3 g (3.6 mmole) of freshly distilled, colorless diketene and 5 ml of toluene. Then, 0.2 ml of N,N,N',N'-tetramethylethylenediamine was added to the resulting pale yellow solution, in one portion. The solution, which immediately became brighter yellow, was refluxed for 16 hours in a reaction vessel equipped with a Dean Stark trap, then was cooled. Subsequent stirring of the solution at room temperature for one hour resulted in the appearance of a crystalline precipitate. The reaction mixture was placed in a freezer (−18° C.) for about 2 hours, then was filtered. The solid obtained in this manner was washed with toluene until colorless and then air dried to give 0.74 g (61% yield) of 4-acetyl-5,6-bis(p-chlorophenyl)-2H-pyridazin-3-one, melting at 269°-270° C. A small additional amount of product was recovered from the filtrate.

EXAMPLE 12

4-Acetyl-5,6-bis(p-chlorophenyl)-2H-pyridazin-3-one (3.1 g), ethylene carbonate (2.0 g), and potassium hydroxide (powdered) were dissolved in dimethylformamide (50 ml) and the flask placed in an oil bath (110°-120° C.) until $CO_2$ evolution ceased (ca. 3.5 hours). The reaction mixture was poured into water (400 ml) and chilled at 5° C. for 1 hour. The resulting precipitate was separated by filtration and recrystallized from methanol (85 ml) to afford 4-acetyl-5,6-bis(p-chlorophenyl)-2-(2'-hydroxyethyl)-2H-pyridazin-3-one (68 percent yield) as pale yellow crystals, m.p. 191°-193° C.

Analysis—calculated for $C_{20}H_{16}Cl_2O_3$ (%): C, 59.56; H, 4.00; N, 6.95. Found (%): C, 59.44; H, 3.94; N, 6.71.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A process for the preparation of a compound of the general formula

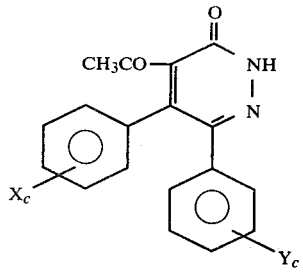

wherein $X_c$ and $Y_c$ are the same or different and are independently selected from the group consisting of halogen, $C_1$–$C_4$ alkyl and $C_1$–$C_4$ alkoxy where c is 0, 1 or 2; which comprises reacting a monohydrazone of the formula

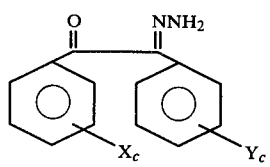

wherein $X_c$ and $Y_c$ are defined as above, with diketene.

2. A process according to claim 1 wherein the reaction is carried out in suitable organic solvent.

3. A process according to claim 2 wherein the solvent is xylene.

4. A process according to claim 2 wherein the solvent is toluene.

5. A process according to claim 1 wherein the reaction is carried out in the presence of a suitable basic catalyst.

6. A process according to claim 5 wherein the catalyst is triethylamine.

7. A process according to claim 5 wherein the catalyst is tetramethylethylenediamine.

8. A process according to claim 1 wherein the reaction is carried out at elevated temperature.

9. A process according to claim 8 wherein the reaction is carried out at reflux temperature.

10. A process according to claim 1 wherein $X_c$ and $Y_c$ are para-halo.

11. A process according to claim 1 wherein the monohydrazone is p,p'-dichlorobenzil monohydrazone.

12. A process for the preparation of 4-acetyl-5,6-bis(p-chlorophenyl)-2H-pyridazin-3-one which comprises reacting p,p'-dichlorobenzil monohydrazone with diketene in a suitable organic solvent at elevated temperature.

13. A process according to claim 12 wherein the solvent is xylene or toluene.

14. A process according to claim 12 wherein the reaction is carried out in the presence of a suitable basic catalyst.

15. A process according to claim 14 wherein the catalyst is triethylamine or tetramethylethylenediamine.

16. A process according to claim 12 wherein the reaction is carried out at reflux temperature.

17. A process according to claim 12 wherein the reaction is carried out in xylene solvent, at reflux temperature, in the presence of triethylamine catalyst.

18. A process according to claim 17 wherein triethylamine is present at a level of between about 0.1 and about 0.3 ml/g of monohydrazone.

19. A process according to claim 18 wherein triethylamine is present at a level of about 0.2 ml/g of monohydrazone.

20. A process according to claim 19 wherein the reaction mixture is refluxed for about 2 hours.

21. A process according to claim 2, 3, 4, 12, 13, 14, 15, 16, 17, 18, 19 or 20 wherein the monohydrazone reactant is first combined with the organic solvent, and the diketene reactant is subsequently added close to the surface of the reaction liquid.

* * * * *